United States Patent [19]

Hürlimann

[11] Patent Number: 5,235,193
[45] Date of Patent: Aug. 10, 1993

[54] DEVICE FOR IDENTIFYING A CONTAINER CARRIER FOR AN AUTOMATIC ANALYTICAL APPARATUS WITH FACETED LIGHT GUIDING PLATE

[75] Inventor: Hans-Jörg Hürlimann, Hünenberg, Switzerland

[73] Assignee: Hoffman-La Roche Inc., Nutley, N.J.

[21] Appl. No.: 787,453

[22] Filed: Nov. 4, 1991

[30] Foreign Application Priority Data

Nov. 13, 1990 [CH] Switzerland ............. 3591/90

[51] Int. Cl.⁵ ............................................. G06K 7/10
[52] U.S. Cl. ............................ 250/566; 250/227.31
[58] Field of Search .......... 250/566, 568, 569, 227.31, 250/227.32; 359/742, 641

[56] References Cited

U.S. PATENT DOCUMENTS

| 659,353 | 10/1900 | Pitkin | 359/742 |
|---|---|---|---|
| 3,248,554 | 12/1961 | Chen . | |
| 3,375,348 | 3/1968 | Goldstern | 250/568 |
| 3,390,399 | 6/1968 | Leonard | 359/742 |
| 3,897,216 | 6/1975 | Jones . | |
| 4,057,148 | 11/1977 | Meyer et al. . | |
| 4,076,384 | 2/1978 | Deml et al. | 359/742 |
| 4,114,045 | 9/1978 | Shiina . | |

FOREIGN PATENT DOCUMENTS 896280 1/1960 United Kingdom .
1429052 3/1976 United Kingdom .

*Primary Examiner*—David C. Nelms
*Attorney, Agent, or Firm*—George M. Gould; George W. Johnston

[57] ABSTRACT

A device for identifying a container carrier for an automatic analytical apparatus is described. The carrier has an array of fields on a flange, some of the fields being transparent and the other fields being opaque. The device includes an electro-optical arrangement to detect whether each of the fields is transparent or opaque. The electro-optical arrangement having a light source, a light guide member for receiving a beam of light from the light source and splitting the beam into a plurality of light rays, each ray being directed toward one of the fields, and a plurality of light receivers each being respectively associated with each of the fields and being disposed so as to receive the ray of light which passes through the associated field.

4 Claims, 8 Drawing Sheets

5,235,193

DEVICE FOR IDENTIFYING A CONTAINER CARRIER FOR AN AUTOMATIC ANALYTICAL APPARATUS WITH FACETED LIGHT GUIDING PLATE

FIELD OF THE INVENTION

This invention is concerned with a device for identifying a container carrier for an automatic analytical apparatus, the carrier having an array of fields on a flange, some of the fields being transparent and the other fields being opaque, the device also containing an electro-optical arrangement to detect whether each of the fields is transparent or opaque.

The invention is further concerned with an automatic analytical apparatus for analyzing biological samples placed in the apparatus in sample containers, a plurality of sample containers being carried by a carrier, the carrier having an array of fields on a flange, some fields being transparent and some fields being opaque, the apparatus comprising a device for identifying a container carrier, which device includes an electro-optical arrangement to detect whether each of the fields is transparent or opaque.

BACKGROUND

In known devices of this kind, a light source and a light receiver are provided for each field and are disposed on opposite sides of the field. A ray of light generated by the light source is directed towards the field. If the field is transparent, the ray of light meets the light receiver which generates a corresponding output signal. Otherwise there is no output signal. In this way the rack can be identified by means of a binary code.

A considerable disadvantage of the prior art device is that the absence of an output signal from a light receiver may be due not only to the scanning of an opaque field but also may be caused by a defective light source. This results in considerable uncertainty in identifying the container carrier. In many applications such uncertainty cannot be tolerated. This is particularly the case in the identification of carriers for containers for biological specimens in automatic analytical systems of the kind used in medical diagnostic laboratories.

The object of the invention, therefore, is to obviate the above disadvantage.

SUMMARY OF THE INVENTION

According to the invention, there is provided an improved device of the type referred to earlier, said device being characterized in that the electro-optical arrangement comprises the following components:
a) a light source;
b) a light guide means for receiving a beam of light from the light source and splitting said beam into a plurality of light rays, each ray being directed toward one of the fields; and
c) a plurality of light receivers each being respectively associated with each of the fields and being disposed so as to receive said ray of light which passes through said associated field.

The particular advantages of the invention are that the reliability of the device for identifying the container carrier is greater because any breakdown of a single light source will reliably be detected as a system fault which is impossible where several light sources are used. The use of a single light source also reduces the material expense.

One advantageous embodiment of the invention is characterized in that the light guide comprises a light guiding plate having a light entry at one end and a light exit at the other end, in that the light guiding plate has an internally reflecting surface situated opposite the light entry and inclined to the longitudinal axis of the light guiding plate, and in that the light exit is a wall which, in order to produce an axis-parallel ray exit, comprises wall segments forming angles with a plane normal to the longitudinal axis (Y—Y) of the light guiding plate, the size of said angles increasing with the distance of the wall segment from the longitudinal axis of the light guiding plate.

This embodiment of the invention is distinguished by a simple and hence more reliable and relatively inexpensive construction of the light guide.

An apparatus according to the invention is characterized in that it comprises a device of the above defined type for identifying a container carrier placed in the apparatus.

BRIEF DESCRIPTION OF THE DRAWINGS

One exemplified embodiment of the invention is described hereinafter with reference to the accompanying drawings wherein.

DETAILED DESCRIPTION OF THE INVENTION

The present invention is directed to a device for identifying a container carrier in an automatic analytical apparatus. The carriers of the automatic analytical apparatus have an array of specimen fields, some fields being transparent and some fields being opaque. The present invention comprises a light source; a light guide for receiving a beam of light from the light source and splitting the beam into a plurality of light rays, each ray being directed toward one of the fields; and a plurality of light receivers each being respectively associated with each of the fields and being disposed so as to receive the ray of light which passes through the associated field.

The present invention is further directed to a light guide which splits the beam of light from the source into a plurality of rays. The light guide of the invention comprises a light guiding plate having a light entrance end and a light exit end. The light beam from the source entering the plate is then internally directed from the entrance end to the exit end. The exit end is formed with a plurality of segments, or facets, each facet is configured and dimensioned so as to refract the internal light into the plurality of light rays and to direct the rays respectively toward each of the fields.

Figure 1:
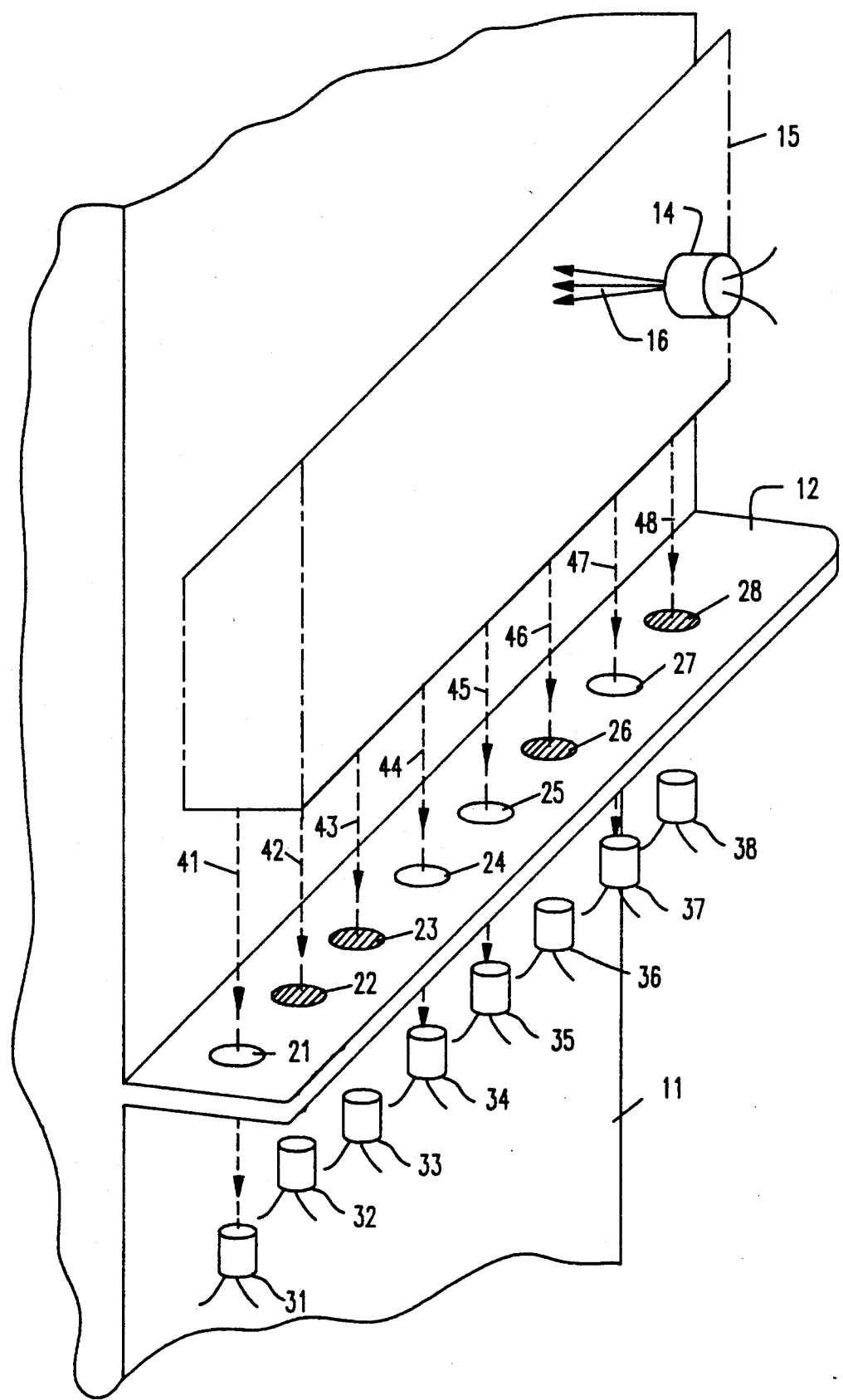
FIG. 1 is a diagrammatic perspective view of a device according to the invention for the identification of a container carrier.

With reference to FIG. 1, a diagrammatic perspective view is shown of a device according to the invention for the identification of a container carrier 11 used in an automatic analytical apparatus to accommodate sample containers which contain biological specimens. The specimens are examined in the analyzer using e.g. suitable analytical methods. The carrier 11 has a flange 12 which contains an array of fields 21-28, some of which, e.g. fields 21, 24, 25, 27 are transparent, while the remainder 22, 23, 26, 28 are opaque. A transparent field may e.g. be formed by an opening at a specific location of the flange 12. Conversely, the absence of such an opening at a specific location of the flange 12 may form an opaque field. The device shown in FIG. 1 also comprises an electro-optical device to detect whether each of the fields 21-28 is transparent or opaque. The electro-optical device comprises the following components: a single light source 14, a plurality of light receiver 31-38, each associated with one of the fields, and a light guide 15 which is shown diagrammatically in FIG. 1 and which, from a beam of light 16 generated by the light source 14, generates a plurality of rays of light 41-48 each directed towards one of the fields 21-28 and reaching the associated light receiver 31, 34, 35, 37 through the transparent fields 21, 24, 25, 27.

Figure 2:
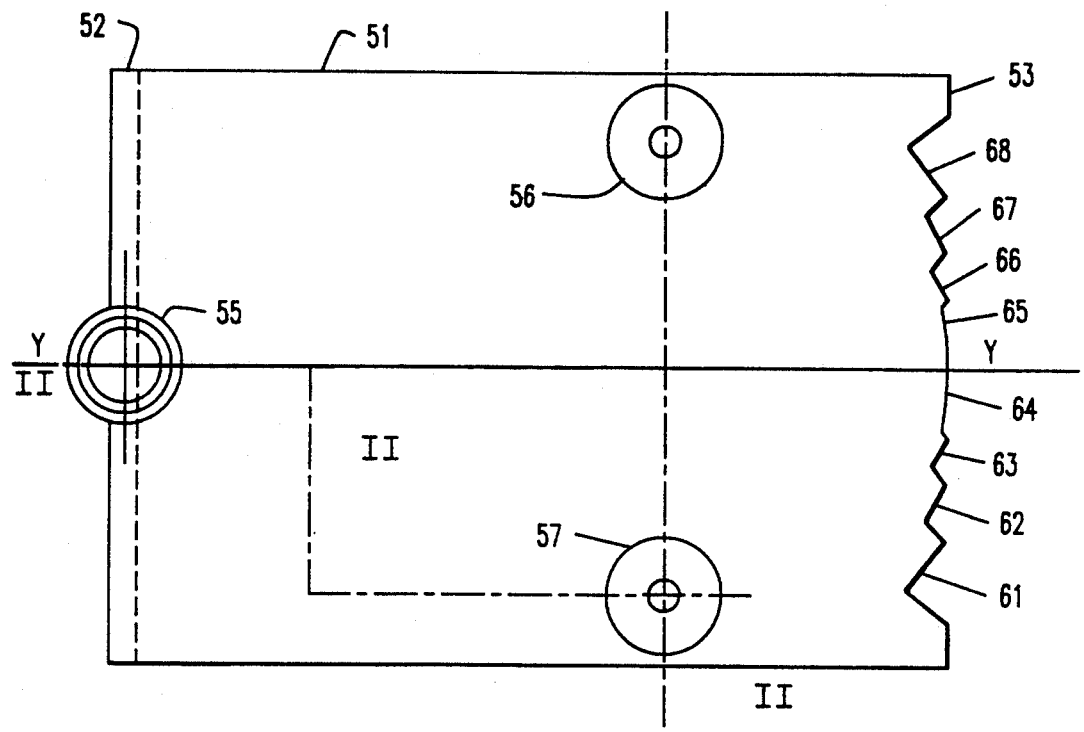
FIG. 2 is a bottom plan views of a light guiding plate of the light guide in FIG. 1, and of the elements associated therewith.
Figure 3:
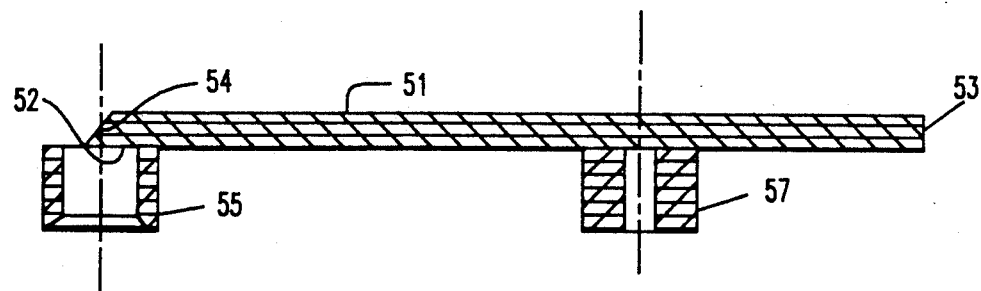
FIG. 3 is a cross-section of the arrangement shown in FIG. 2 on the line II—II.

In a preferred embodiment of the invention, a light guiding plate 51 shown in FIGS. 2 and 3 is used as the light guide. The light guiding plate 51 has a light entry 52 at one end and a light exit 53 at the other end. The photo-conductive plate 51 has an inwardly reflecting surface 54 situated opposite to the light entry 52, the surface 54 being inclined to the longitudinal axis of the plate 51. The light exit 53 is a wall comprising flat wall segments, or facets, 61-68 forming angles to a plane normal to the longitudinal axis Y—Y of the light guiding plate, the magnitude of the angles increasing with the distance of the wall segment from the longitudinal axis Y—Y of the plate 51.

The bottom wall of the light guiding plate 51 is secured with a suitable adhesive to three cylindrical carrier elements 55, 56, 57. A light-emitting diode (LED) used as light source is disposed in a cavity of the carrier element 55.

The light guiding plate 51 is made, for example, from polymethylmethacrylate (PMMA). Alternatively it may consist of another plastic with similar optical properties of glass. An important factor in the selection of the material for the light guiding plate is that it should allow good light transmission and no reflection losses at the wavelength of the light source used. The wall 53, or at least its segments 61-68, are polished.

Figure 4:
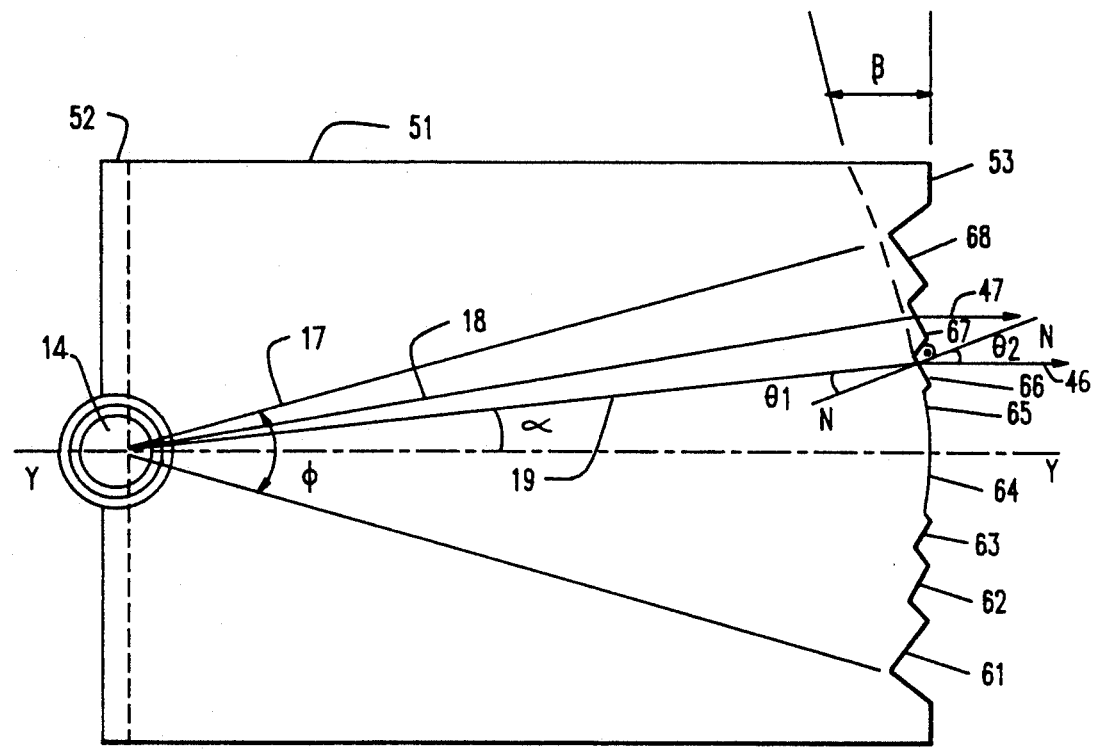
FIG. 4 is a bottom plan view of the light guiding plate of FIG. 2 additionally showing a beam of light generated by a light source and the path of the rays of light.
Figure 5:
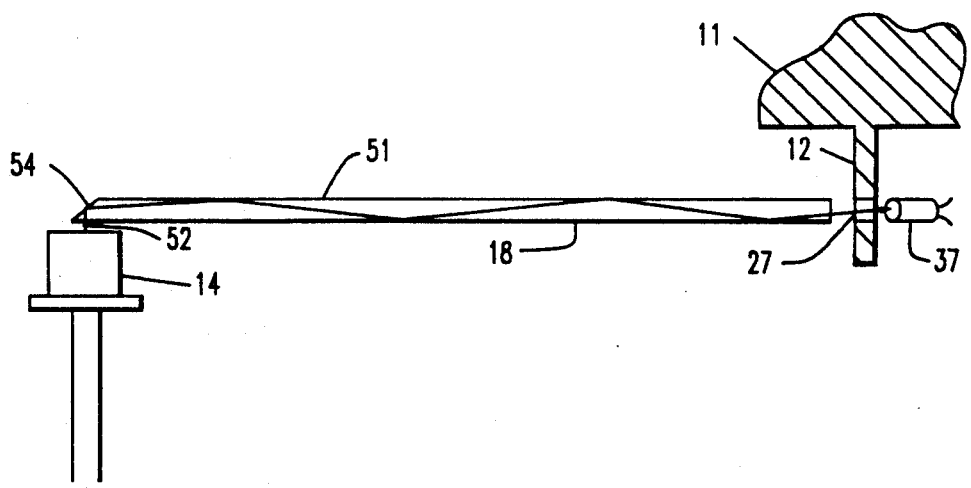
FIG. 5 is a diagrammatic side view of the light guiding plate of FIG. 2 showing the path of a ray of light.

FIGS. 4 and 5 diagrammatically show the path of the rays of light in the light guiding plate 51. The light source 14 emits the beam of light 16 shown in FIG. 1, this beam passing through the light entry 52 into the light guiding plate 51 and being reflected therein at the reflecting surface 54. As will be seen from FIG. 4, this produces a beam of light 17 having an aperture angle $\phi$. Two rays 18 and 19 of the beam 17 are shown in FIG. 4. As shown for ray 18 in FIG. 5, the rays of light of the beam 17 meet the top and bottom walls of the light guiding plate 51 at so shallow an angle that total reflection occurs. The light therefore cannot leave the light guiding plate 51 through these walls. As shown in FIG. 5, each ray of the beam 17 is thus reflected from wall to wall until it meets the wall 53 consisting of segments. FIG. 4 shows the axis of incidence N—N. Rays of light, which, like 18 and 19 in FIG. 4, meet a wall segment, such as 66 or 67, practically perpendicularly, are refracted and leave the light guiding plate 51 in a direction approximately parallel to the longitudinal axis Y—Y of the light guiding plate 51. In FIG. 4 this is shown for the rays 46 and 47 formed by refraction of the rays 19 and 18. The rays emerging from the wall segments 61-68 meet their associated fields 21-28 shown in FIG. 1. If the field is transparent, the ray of light meets a light receiver associated with the field. In this way, for example, ray 18 in FIGS. 4 and 5 meets the light receiver 37.

To achieve the above-described path for the rays of light emerging through the wall segments, or facets, 61-68, the wall segments must have a selected position as required for this. To this end, the refractive index of the material of the light guiding plate 51 with respect to air and the law of refraction are taken into account to calculate the angle $\beta$ which each wall segment should form with a plane perpendicular to the longitudinal axis Y—Y. According to the law of refraction the relationship between the angles $\theta_1$ and $\theta_2$ shown in FIG. 4 is defined by the equation $n_1 \sin \theta_1 = n_2 \sin \theta_2$, wherein $n_1$ is the refraction index of the material of the light guiding plate 51 and $n_2$ is the refraction index of the air surrounding this plate. When the light guiding plate 51 is made of PMMA $n_1 = 1.492$. Air has the refraction index $n_2 = 1$. In addition from FIG. 4 it can be appreciated that $\beta = \theta_2$ and that $\theta_1 = \theta_2 - \alpha$, wherein $\alpha$ is the angle comprised between the longitudinal axis of the light guiding plate 51 and the beam 19 which falls on the center of the wall segment 66. The value of the angle $\beta$ which defines the angular position of a given wall segment, e.g. segment 66, is calculated by the formula $$\beta = \arctan [\sin \alpha / (\cos \alpha - n_2/n_1)].$$

Figure 6:
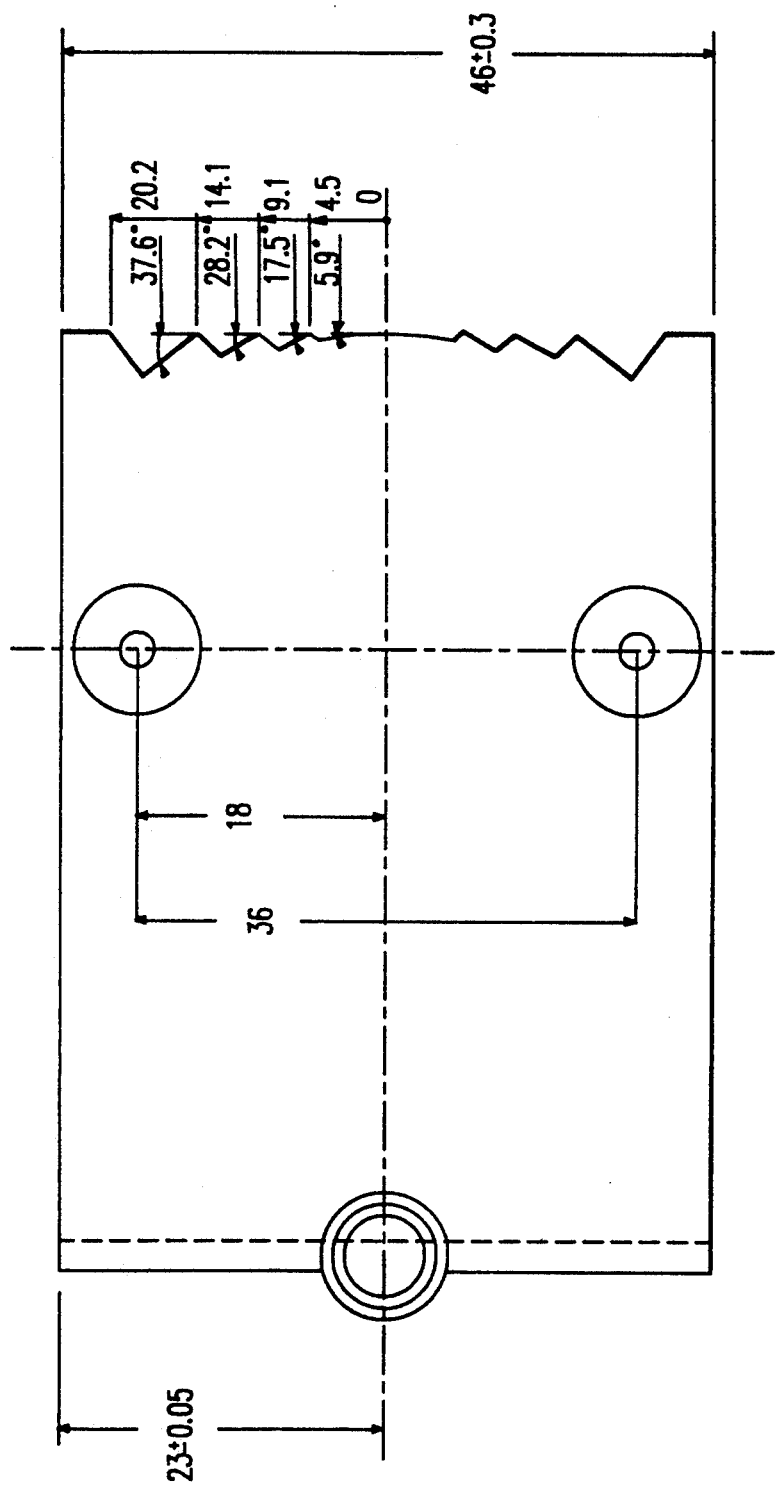
FIG. 6 is the bottom plan view of light guiding plate of FIG. 2 additionally showing some of the dimensions of one embodiment of the light guiding plate in millimeters.
Figure 7:
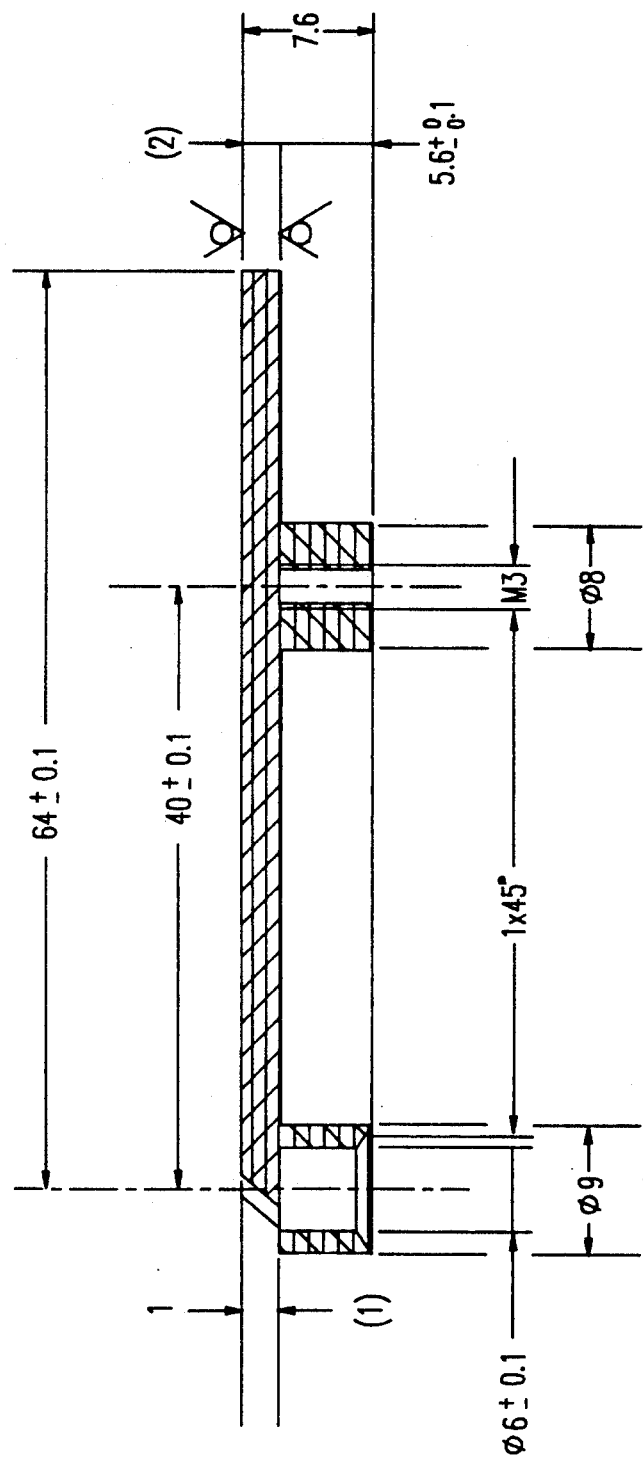
FIG. 7 is the cross-section of FIG. 3 additionally showing certain dimensions of one embodiment of the light guiding plate in millimeters.

FIG. 6 indicates, as an example, angles determined in connection with the wall segments 65-68 in FIG. 4 for a light guiding plate 51 made from polymethylmethacrylate (PMMA) and some of the dimensions of one exemplified embodiment of this plate in millimeters. Other dimensions of the same plate are indicated in millimeters in FIG. 7. The width required for the light guiding plate 51 is governed largely by the width of the array of fields 21-28 in the container carrier 11. The length required for the light guiding plate 51 is governed basically by its width and by the aperture angle $\phi$ of the beam of light 17 in FIG. 4. This aperture angle is determined by the aperture angle (radiation characteristic) of the light source 14. Selection of a suitable thickness for the light guiding plate 51 must take into account the fact that it should be small enough for the above-mentioned total reflection to occur. On the other hand, for good utilization of the energy emitted by the light source, the largest possible proportion of the beam of light 16 emitted by the light source 14 should enter the plate. To this end, the thickness of the plate and a suitable light source must be selected to generate a beam of light having an aperture angle adapted to the thickness of the plate so that the maximum proportion of the beam of light meets the surface 54.

In the present exemplified embodiment, the light source 14 used was a light-emitting diode manufactured by Siemens under the name SFH 485P and the light receiver 31-38 was a matching element, e.g. an NPN silicon photo-darlington designated OP300 manufactured by the Optoelectronics Division of TRW Electronic Components Group.

Figure 8:
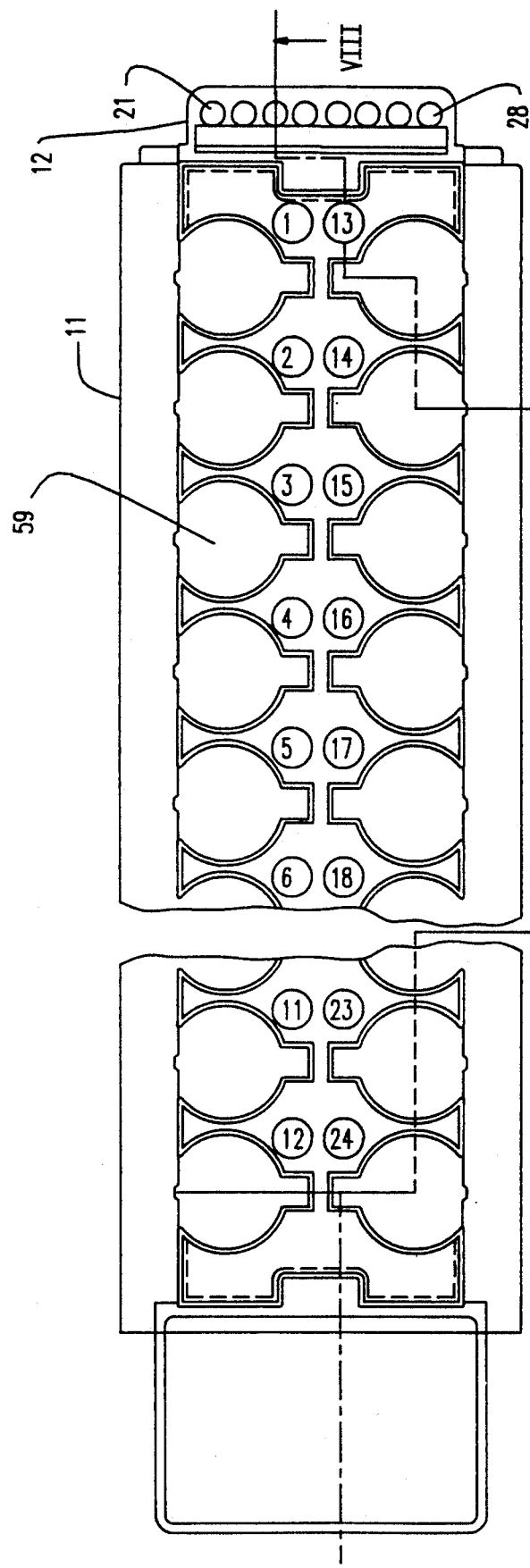
FIG. 8 is a plan view of a container carrier for an automatic analytical system.

Referring to FIG. 8, a plan view of a container carrier 11 is shown for an automatic analytical system used, for example, in a medical diagnostic laboratory. This carrier has a number of chambers 59 to receive containers, e.g. containers for biological specimens. A flange 12 of the carrier 11 has an array of fields 21-28, each of which is formed with or without an opening in order to define a binary code and hence allow identification of the carrier. A carrier of this kind can be identified by means of the above described device.

Figure 9:
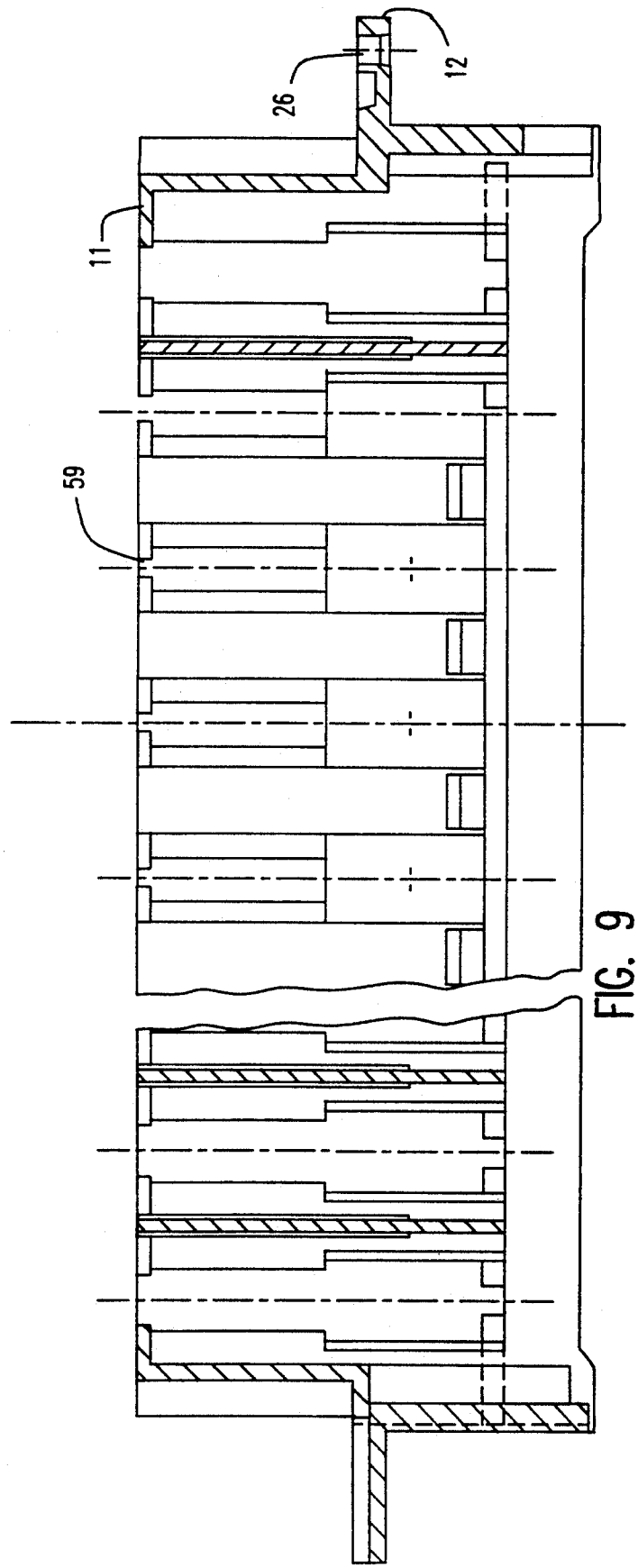
FIG. 9 is a cross-section of the portions of the container carrier cut by the plane segments represented by the line VIII—VIII shown in FIG. 8.

FIG. 9 is a cross-section of the portions of the container carrier 11 cut by the plane segments represented by the segmented line VIII—VIII shown in FIG. 8. Some segments of this line are parallel to the longitudinal axis of the container carrier and other segments are perpendicular to that axis.

Figure 10:
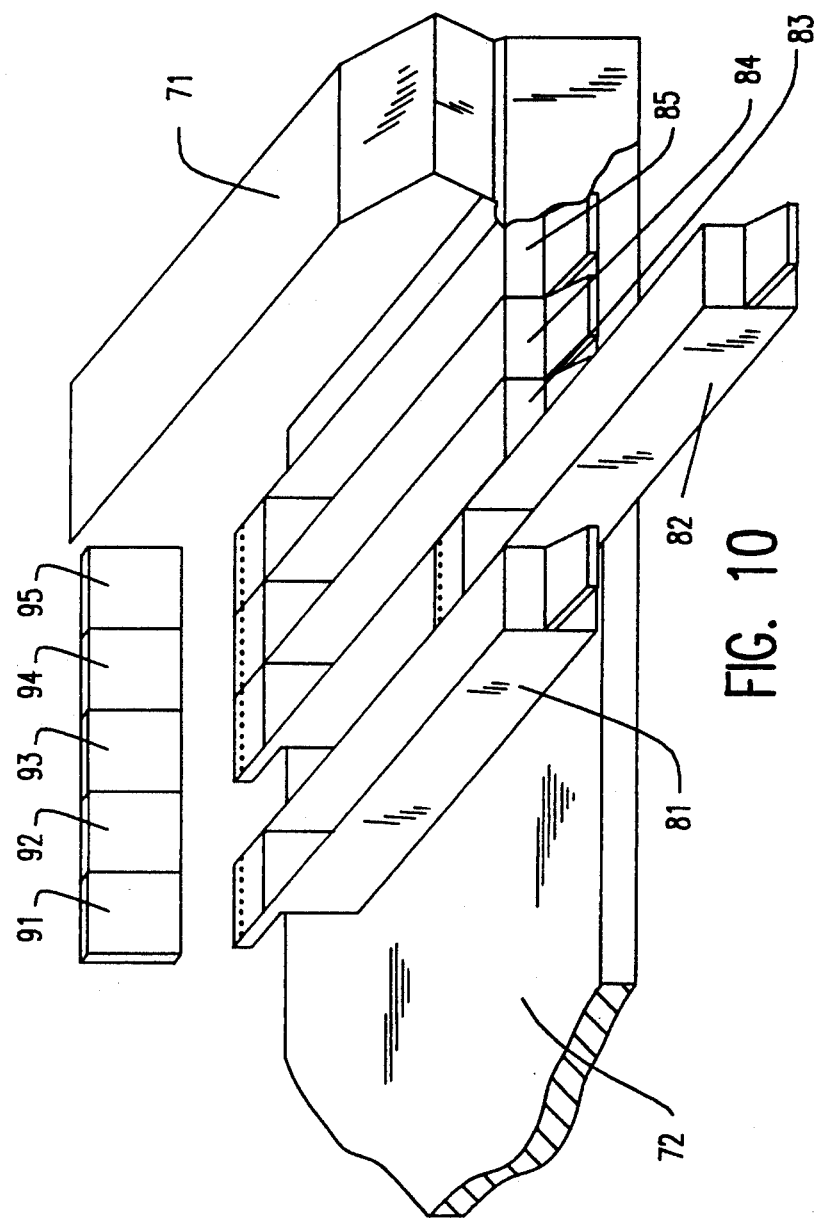
FIG. 10 represents a diagrammatic, perspective view of part of an analytical apparatus in accordance with the invention.

FIG. 10 schematically shows part of an apparatus according to the invention. This apparatus is apt to be used for automatically analyzing test specimens placed in respective speciment containers. A group of said containers being disposed in a container carrier. The apparatus has an area 72 in which a plurality of container carriers 81-85, carrying each a group of specimen containers, are placed during the analysis of the specimens.in the apparatus. The container carriers 81-85 are e.g. as described above with reference to FIGS. 8 and 9. As shown in FIG. 10 the apparatus further includes a plurality of light guiding plates 91-95 corresponding each to one of the container carriers 81-85. Each of the light guiding plates 91-95 forms part of an electro-optical arrangement for detecting whether each of the fields on a flange of a carrier is transparent or opaque and thereby for enabling an identification of said carrier. Such an electro-optical arrangement is as described above with reference to FIGS. 1-7. Each of the light guiding plates 91-95 has the same structure and function as light guiding plate 51 described above with reference to FIGS. 2-7.

What is claimed is:

1. A device for identifying a container carrier in an automatic analytical apparatus, the carrier having an array of fields on a flange, some fields being transparent and some fields being opaque; the device including an electro-optical arrangement to detect whether each of the fields is transparent or opaque, the electro-optical arrangement comprising:
   a) a light source;
   b) a light guiding plate having a light entrance end and a light exit end and means for internally directing the light beam of the light source from said entrance end to said exit end; said exit end being formed with a plurality of facets, each facet configured and dimensioned so as to refract the internal light and to direct thereby a refracted light ray toward one of the fields, the dimensions and the material of the light guiding plate being so chosen that along the light path substantially no reflection losses occur between the light entrance and the light exit end, and
   c) a plurality of light receivers each being respectively associated with each of the fields and being disposed so as to receive said ray of light which passes through said associated field.

2. The device according to claim 1, wherein said facets form different angles with a plane normal to the light guiding plate and to its longitudinal axis, the size of said angles increasing with the distance of the facet from the longitudinal axis of the light guiding plate.

3. An automatic analytical apparatus for analyzing biological samples placed in the apparatus in sample containers, a plurality of sample containers being carried by a carrier, the carrier having an array of fields on a flange, some fields being transparent and some fields being opaque, the apparatus comprising a device for identifying a container carrier, which device includes an electro-optical arrangement to detect whether each of the fields is transparent or opaque, the electro-optical arrangement comprising:
   a) a light source;
   b) a light guiding plate having a light entrance end and a light exit end and means for internally directing the light beam of the light source from said entrance end to said exit end; said exit end being formed with a plurality of facets, each facet configured and dimensioned so as to refract the internal light and to direct thereby a refracted light ray toward one of the fields, the dimensions and the material of the light guiding plate being so chosen that along the light path substantially no reflection losses occur between the light entrance and the light exit end, and
   c) a plurality of light receivers each being respectively associated with each of the fields and being disposed so as to receive said ray of light which passes through said associated field.

4. An automatic analytical apparatus according to claim 3, wherein said facets form different angles with a plane normal to the light guiding plate and to its longitudinal axis, the size of said angles increasing with the distance of the facet from the longitudinal axis of the light guiding plate.

* * * * *